United States Patent [19]

Adachi

[11] 4,455,380

[45] Jun. 19, 1984

[54] PROCESS FOR DETERMINING TUMOR-ASSOCIATED GLYCOLINKAGE

[75] Inventor: Masakazu Adachi, Gunma, Japan

[73] Assignee: Otsuka Pharmaceutical Co., Ltd., Tokyo, Japan

[21] Appl. No.: 344,151

[22] Filed: Jan. 29, 1982

[51] Int. Cl.³ .................... G01N 33/56; G01N 33/58; G01N 33/60; G01N 33/68

[52] U.S. Cl. .................... 436/504; 436/501; 436/63; 436/64; 436/94; 436/808; 436/813; 435/4; 435/188; 260/112 R; 422/61

[58] Field of Search .................... 424/1, 1.5; 436/501, 436/503, 504, 63, 64, 94, 804, 808, 813, 811, 827; 435/4, 188; 260/112 R; 422/61

[56] References Cited

U.S. PATENT DOCUMENTS

| | | | |
|---|---|---|---|
| 4,146,603 | 3/1979 | Davidson et al. | 424/1 |
| 4,289,747 | 9/1981 | Chu | 424/1 |
| 4,334,017 | 6/1982 | Plotkin et al. | 435/7 |
| 4,389,392 | 6/1983 | Adachi | 424/1 |

FOREIGN PATENT DOCUMENTS

| | | |
|---|---|---|
| 54-009435 | 3/1980 | Japan . |
| 54-141741 | 3/1980 | Japan . |
| 56-154660 | 11/1981 | Japan . |
| 57-29950 | 2/1982 | Japan . |
| 57-29951 | 2/1982 | Japan . |
| 2043890 | 10/1980 | United Kingdom . |

*Primary Examiner*—Benjamin R. Padgett
*Assistant Examiner*—M. Moskowitz
*Attorney, Agent, or Firm*—Sughrue, Mion, Zinn, Macpeak, and Seas

[57] ABSTRACT

A process for determining the level of TAG in a sample of body fluid which comprises reacting the TAG in a sample of body fluid with an AG-binding lectin or L-fucose-binding lectin to form a TAG-lectin complex and measuring the amount of the TAG-lectin complex or an unreacted lectin is disclosed. The process shows low cross-reactivity with hepatic diseases and is useful for diagnosis of cancers.

32 Claims, 18 Drawing Figures

TAG LEVELS OF HEALTHY PERSONS

TAG LEVELS OF PATIENTS WITH DISEASES OTHER THAN CANCERS

PROCESS FOR DETERMINING TUMOR-ASSOCIATED GLYCOLINKAGE

BACKGROUND OF THE INVENTION

The present invention relates to a process for determining tumor-associated glycolinkage (hereunder referred to as TAG) in the body fluid of mammals, more particularly, TAG including glycoproteins, glycopeptides, glycolipids and/or sugars having a certain specific terminus which increases with the proliferation of undifferentiated cells, particularly tumorous or cancerous cells.

Methods are known for diagnosing cancer by measuring a specific glycoprotein which is specifically produced in patients with cancer. Most of these methods utilize the antigenicity of protein moiety of the glycoprotein; for example, a method for diagnosing primary liver cancer by measuring $\alpha_1$-fetoprotein and a method for diagnosing cancer of a digestive organ, particularly rectal cancer, by measuring CEA are known (*Igaku no Ayumi* (*Progress in Medicine*), 106, 5, Fifth Saturday Special Issue, pp. 235–250 (1978)). But these diagnostic methods are coparatively limited in their applicability.

Further investigations have revealed that the body fluid of a patient with cancer contains TAG produced by undifferentiated cells (mostly cancerous cells) and released into the body fluid, and that such TAG differs considerably from the sugars produced by differentiated cells (mostly normal cells) and released into the body fluid with respect to the sugar chain structure, sugar chain length and kind of constituent sugar residue. It has also been found to determine the level of TAG in a sample of body fluid which comprises reacting the TAG in a sample of body fluid with a lectin which can specifically bind with galactose-($\beta 1 \rightarrow 3$ or $\oplus 1 \rightarrow 4$)-N-acetylglucosamine and/or galactose-($\beta 1 \rightarrow 3$ or $\beta 1 \rightarrow 4$)-N-acetylgalactosamine terminus (GB-2043890A, U.S. patent application Ser. No. 187,890, filed on Sept. 17, 1980).

In view of increasing desire for obtaining methods of measuring the level of TAG and diagnostic methods which are less limited in their applicability and have improved sensitivity extensive investigations have been made, and as a result found that TAG contains glycoproteins, glycopeptides, glycolipids and/or sugars having N-acetyl-D-galactosamine (hereunder referred to as AG) or L-fucose terminus, that it is specifically bound with certain kinds of lectins (hereunder a lectin which can be bound specifically with AG terminus is referred to as AG-binding lectin and that which can be bound specifically with L-fucose terminus is referred to as L-fucose-binding lectin), and that therefore, by reacting the TAG in the body fluid with an AG-binding lectin or L-fucose-binding lectin (hereunder both the lectins sometimes are referred to as specific lectin), cancer cells can be detected, the degree of their proliferation can be checked and their growth profile can be known for cancer diagnosis. The present invention has been accomplished on the basis of this finding.

SUMMARY OF THE INVENTION

It is therefore the primary object of the present invention to provide a new process for determining the TAG level of the body fluid. Therefore, this invention provides a process for determining the level of TAG in a sample of body fluid which comprises reacting the TAG in a sample of body fluid with an AG-binding lectin or L-fucose-binding lectin to form a TAG-lectin complex and measuring the amount of the TAG-lectin complex or an unreacted lectin.

BRIEF DESCRIPTION OF THE ACCOMPANYING DRAWINGS

FIGS. 1 and 2 are each a graph showing a standard curve obtained according to one embodiment of the process of the present invention using a competitive reaction process (Example 1(viii) and (ix)).

FIGS. 3 and 3' are graphs showing a calibration curve of one embodiment of the process of the present invention using the competitive reaction process of Example 2(ii).

Figure 7:
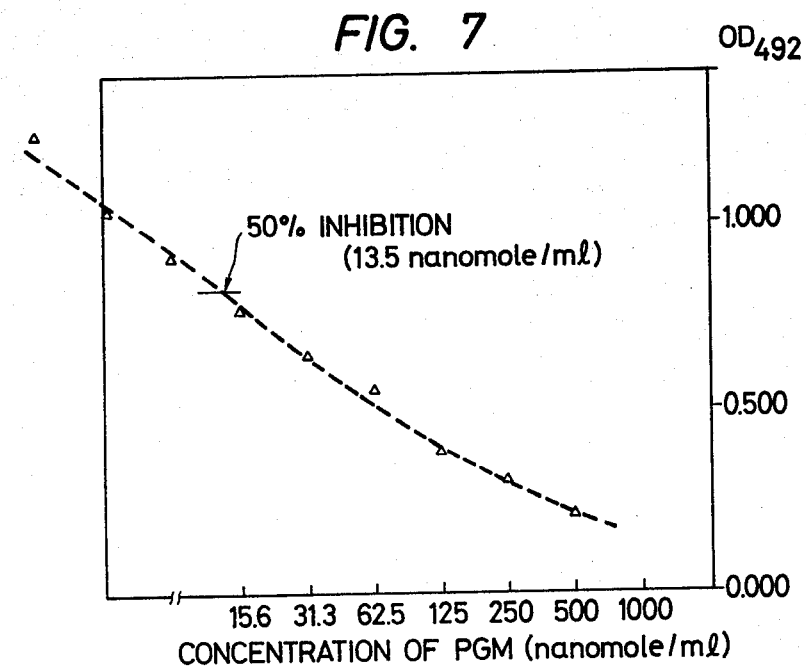
FIG. 7 is a graph showing a calibration curve obtained according to the process of Example 3(iv) using PGM as a standard substance.

FIGS. 8(*a*), (*b*) and (*c*) are graphs showing the level of TAG in samples determined using the calibration curve in FIG. 7.

Figure 9:
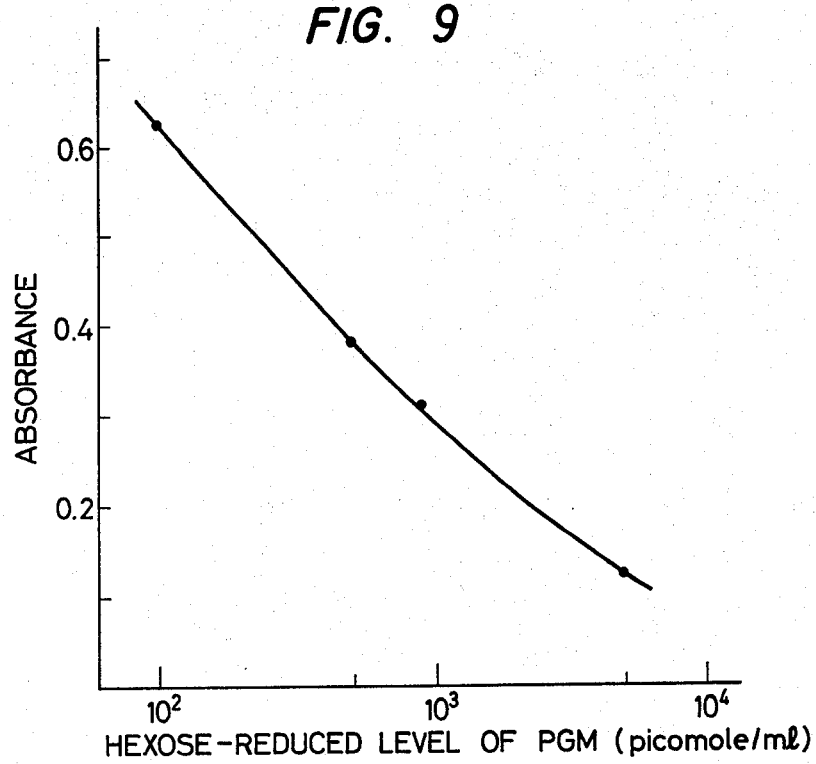
Figure 9:
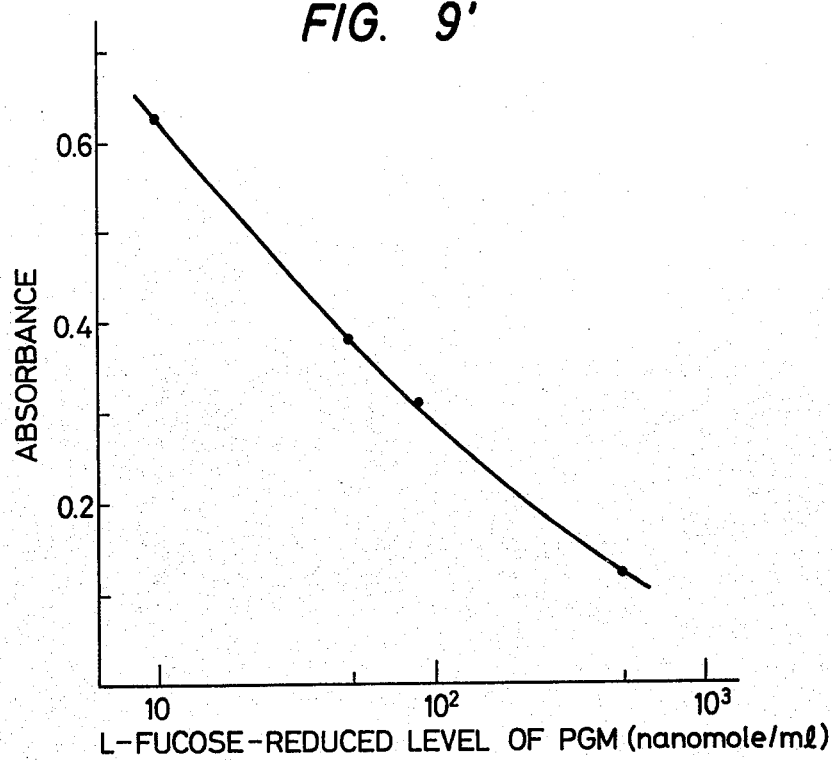

FIGS. 9 and 9' are graphs showing a calibration curve of still another embodiment of the process of the present invention using a competitive reaction process of Example 4(i).

Figure 10:
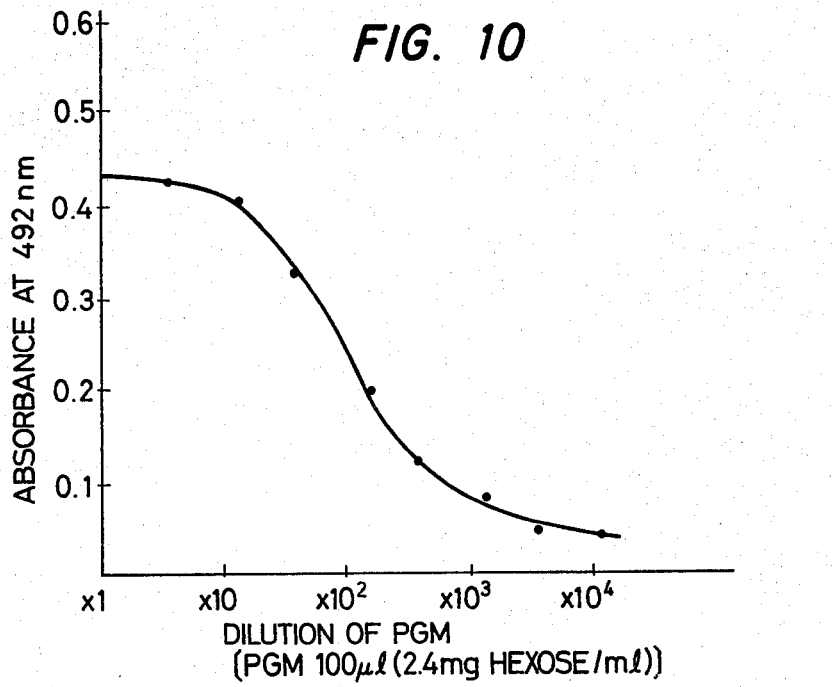

FIG. 10 is a graph showing a calibration curve of a further embodiment of the process of the present invention using a sandwich process of Example 4(ii).

Figure 11:
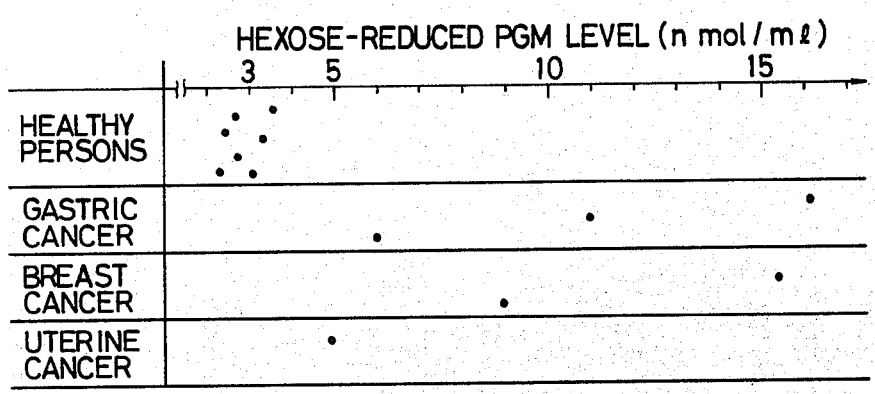

FIG. 11 is a graph showing the level of TAG in healthy persons and patients with various cancers determined by using the competitive process of Example 4(iii).

Figure 12:
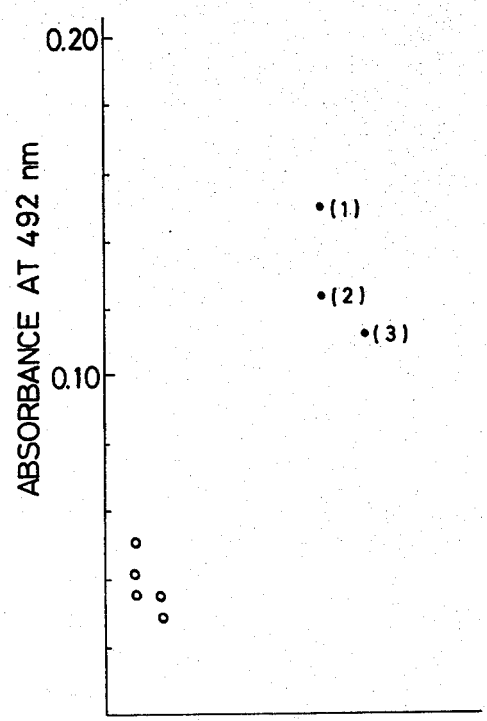

FIG. 12 is a graph showing the level of TAG in healthy persons and patients with various cancers determined by using the process of Example 4(iv).

Figure 13:
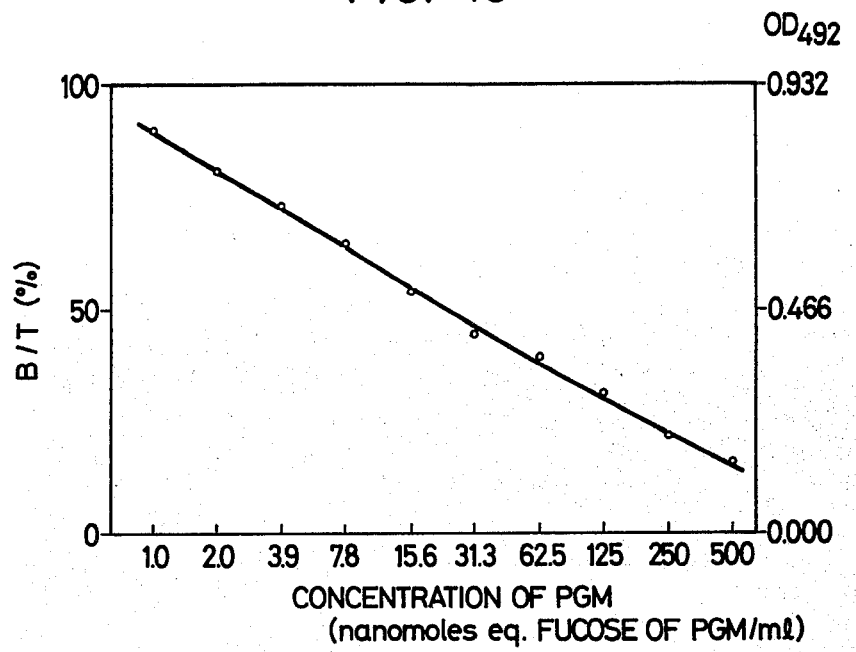

FIG. 13 is a graph showing a calibration curve obtained according to the process of Example 4(v).

Figure 14:
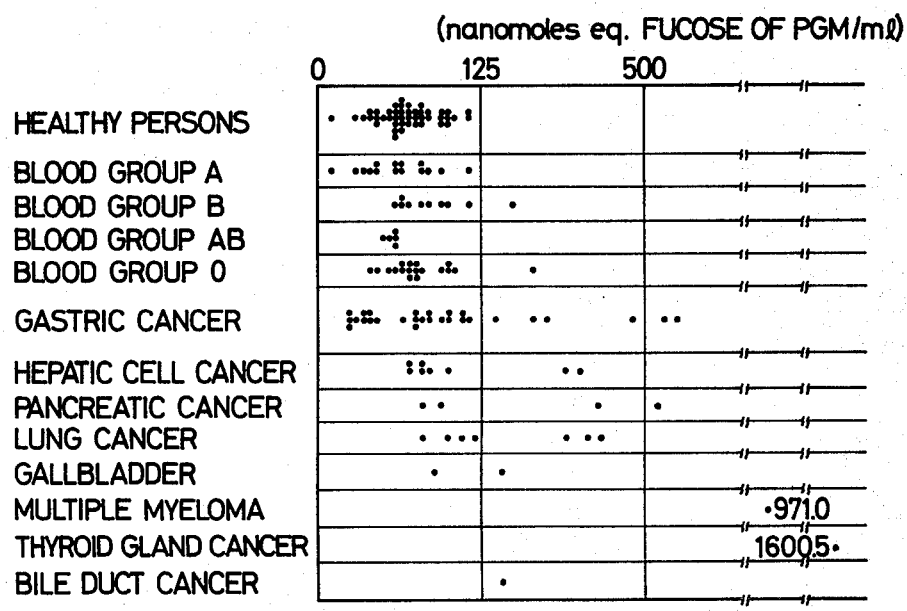

FIG. 14 is a graph showing the level of TAG in samples determined using the calibration curve in FIG. 13.

DETAILED DESCRIPTION OF THE INVENTION

In the present invention, there can be employed various body fluids, among which are blood, cell tissue fluid, lymph fluid, thorax fluid, abdominal fluid, amniotic fluid, gastric juice, urine, pancreatic juice, cerebrospinal fluid, and saliva. Of these, the use of blood in the form of serum or blood plasma is particularly preferred. The quantity of body fluid to be used for the determination ranges from about 0.01 to about 10 ml preferably from 0.1 to 0.2 ml.

According to the present invention, TAG is isolated from the body fluid, is reacted with a specific lectin of the present invention, and the amount of the TAG-bound specific lectin or the residul specific letcin is measured, or alternatively, a specific lectin is labeled and directly added to the body fluid, and the TAG-bound labeled specific lectin or unreacted labeled specific lectin is isolated, and the amount of said TAG-bound labeled specific lectin or unreacted labeled specific lectin is measured. By either method, the TAG level of the body fluid can be determined.

The TAG can be isolated from the body fluid by any of the extraction or separation methods conventionally used to obtain glycoproteins, glycopeptides, glycolipids and/or sugars having AG or L-fucose terminus; among these methods are salting out, precipitation, extraction, centrifugation, dialysis, molecular sieving and inactivation of enzymes. These methods can be used in combination. More specifically, the desired fraction can be prepared by adding sulfosalicylic acid, trichloroacetic acid or zinc sulfate to serum or plasma, or heating the serum or plasma, filtering off the resulting precipitate so as to remove albumin, immunoglobulin, etc., and then dialyzing the residue.

In cases where a labelled specific lectin is used, collected samples of the body fluid except for blood can be directly used as test samples (hereunder referred to as "samples"). But to prevent the denaturation of the samples and accelerate the reaction with the specific lectin, lower-sugar-containing proteins such as bovine serum albumin (BSA) are preferably added as protective proteins. A better result is obtained by adding a suitable amount of protective protein to the sample after removing albumin, immunoglobulin or the like therefrom. When the body fluid is blood, serum obtained by a known serum-collecting method, or plasma obtained by a plasma-collecting method using an anticoagulant such as heparin, EDTA, citric acid or the like can be used as a sample. The particularly preferred sample is a plasma collected and prepared by using heparin as an anticoagulant. If the TAG level is relatively high as in a patient with ascites, these samples may be diluted with a suitable buffer solution as required.

Any AG-binding lectin or L-fucose-binding lectin can be used in the present invention if it is capable of being specifically bound with glycoproteins, glycopeptides, glycolipids and/or sugars having AG or L-fucose terminus. Suitable examples of the AG-binding lectin include Dolichos bean (*Dolichos biflorus*), braid orange lectin, *Helix pomatia* lectin, lima-bean (*Phaseolus limensis*) lectin, soybean (*Glycine max*) lectin and bauhinia bean (*Bauhinia purpurea*) lectin. Suitable examples of the L-fucose-binding lectin include Lotus tetragonolobus lectin [*Brt. J. Enp. Pathi*, 34, 94 (1953)] and Ulex europeus lectin [Boyd., W. C. and Sharpleigh. E., *Blood*, 9, 1195 (1954)].

Various enzymes, fluorescent materials and radioactive materials can be used as the material for labeling the lectin of the present invention. Illustrative examples of the enzymes include glucoamylase, glucose oxidase, peroxidase, alkaline phosphatase, $\beta$-galactosidase, and active fragment of hemoctapeptide, etc.; examples of the fluorescent materials include fluorescein, fluorescein isothiocyanate, rhodamine, dansyl chloride (i.e., 5-dimethylamino-1-naphthalenesulfonyl chloride), etc., and radioactive materials include, for example, radioactive iodine (e.g., $^{125}I$, $^{131}I$, etc.), radioactive tritium, etc.

As will be described hereunder, the specific lectin to be used in the present invention can be labeled with these labeling materials by a method conventionally used to label known proteins such as antigens or antibodies with enzymes, fluorescent materials or radioactive materials.

The process of the present invention is carried out in the following manner: first, a predetermined amount of the body fluid or a TAG fraction is mixed with a labeled or unlabeled specific lectin and the mixture is heated at a temperature lower than 45° C., preferably between 4° and 40° C., more preferably between 20° and 40° C. The resulting TAG-bound labeled or unlabeled specific lectin or the unreacted labeled or unlabeled specific lectin can be isolated by a conventional isolation technique, such as chromatography, electrophoresis, salting out, fractionation, dialysis, gel filtration, adsorption, or combinations thereof. Alternatively, agar gel, agarose gel or polyacrylamide gel may be used as the separating means (see Japanese Patent Application (OPI) No. 151263/80 (the term "OPI" as used herein refers to a "published unexamined Japanese patent application")).

More specifically, the unreacted labeled or unlabeled specific lectin can be isolated by adding to the reaction liquor a suitable amount of a precipitant for a glycoprotein-bound specific lectin such as polyethylene glycol, saturated ammonium sulfate or Rivanol (acrinol); followed by centrifugation or other means to remove the TAG-bound labeled or unlabeled specific lectin. Suitable conditions for the centrifugation can be used depending on the precipitant used; if polyethylene glycol is used as the precipitant, the centrifugation is preferably performed at about 1,000 G for 30 to 60 minutes.

The TAG-bound labeled or unlabeled specific lectin can easily be separated from the unreacted labeled or unlabeled specific lectin by using the difference in diffusion rate on an agar gel, agarose gel or polyacrylamide gel. In particular, if the reaction mixture is put on a gel, the TAG-bound specific lectin does not diffuse and remains on the surface of the gel, whereas the unreacted specific lectin diffuses through the gel. Hence, the TAG-bound specific lectin can easily be separated from the unreacted specific lectin.

The above mentioned gel can be prepared by a conventional method. For instance, a suitable amount of agar, agarose or polyacrylamide is added to a diluent such as distilled water, or diluted citric acid or trishydrochloric acid buffer solution (pH=ca. 7.5), and the mixture is heated at 60° to 80° C. with gentle stirring to form a solution, which is put into a suitable container, such as a test tube, and left to cool until the solution coagulates into a jelly. The concentration of the gel is selected depending upon the size (e.g., molecular weight, stereospecific structure) of the unreacted lectin of the present invention and TAG-bound labeled specific lectin. The gel generally has a concentration of from 0.4 to 2.0 wt%, preferably from 0.7 to 1.0 wt%. If necessary or desired, the gel may contain a preservative. The thus-prepared gel may have a flat surface, but a concave surface is preferred since the resulting complex does not stick to the inside wall of the container.

The TAG level of the body fluid can be calculated from the amount of the isolated TAG-bound labeled or unlabeled specific lectin or unreacted labeled or unlabeled specific lectin as measured by a conventional method.

Various methods can be used to measure the amount of the unlabeled specific lectin that has been unconsumed in the reaction. Preferably, a substance that reacts specifically with the specific lectin to cause agglutination or precipitation is added to the reaction liquor, and the resulting specific change is observed visually or measured by photometric analysis. To state more particularly, the reaction liquor is diluted serially each by 2-fold dilution method with a diluent such as 0.15M phosphate buffer or physiological saline, and a predetermined amount of the dilution is put onto a V-shaped plate, U-shaped plate slide glass or in a small test tube or the like, and a substance that causes a specific agglutination reaction with the specific lectin is added, and the mixture is stirred and left to stand at a temperature lower than 45° C., preferably between 4 and 40° C., for a period of 30 minutes or longer, preferably between 60 and 90 minutes, and the final or maximum degree of dilution at which agglutination occurs is determined. The maximum degree of dilution is defined as the agglutination value. All specific lectins that can be used in the present invention have substantially the same agglutination value.

An example of the substance that causes a specific agglutination reaction with the specific lectin is a glycoprotein having AG or L-fucose terminus. For the AG-binding lectin, Sephadex, latex, glass beads or the like coated with glycoproteins having AAG terminus, such as cytolipins K and R of human erythrocyte membrane, sulfated glycopeptide type A of porcine gastric mucous membrane, asialo derivative of humn blood active substance type A, mucin type A+ of procine submandibular membrane, asialo $GM_1$, and Forssman antigenic substance can be used. For the L-fucose-binding lectin, Sephadex, latex, glass beads or the like coated with glycoproteins having L-fucose terminus, such as human blood active substance type $Le^a$ and $L^b$, sulfated glycoprotein type A of porcine gastric mucous membrane, sulfated glycoprotein active substance type H(O) of porcine gastric mucous membrane and human erythrocyte $H_1$ antigen are used.

When the labeled specific lectin is used, the TAG level can be measured by a suitable method that is selected depending upon the labeling agent for the specific lectin. For example, if the specific lectin is labeled with an enzyme, the TAG level can be determined by measuring the enzymatic activity using a proper enzyme substrate for colorimetric or fluorescence analytic system. If the labeling agent is a fluoroescent material, the TAG level can be determined by measuring the fluorescence intensity, and if the labeling agent is a radioactive material, the TAG level can be determined by measuring the radioactivity. In this manner, the amount of the TAG-bound labeled specific lectin or the unreacted labeled specific lectin can be measured.

A particularly convenient method for carrying out the above-described determination process of the present invention is to use a kit for determining the TAG level of body fluids such as blood plasma or serum. For the purposes of the present invention, a kit containing the specific lectin that can be bound with TAG specifically is used. A stabilizer and/or preservative such as glycerol or bovine serum protein may be added to the specific lectin reagent. The specific lectin reagent may be a lyophilized product, or the kit may contain a water-soluble or water-miscible solvent. Furthermore, the specific lectin reagent may contain a buffer solution for keeping its pH after reconstitution and/or a preservative and/or stabilizer for preventing premature deterioration of the sample. The buffer solution is not essential to the kit, but if it is used at all, its pH is preferably adjusted to from 6 to 7.8. The reconstituting agent preferably contains water, but part or all of the water may be replaced by a water-miscible solvent.

Water-miscible solvents are well known to those skilled in the art, and suitable examples thereof include glycerol, alcohols, glycols, and glycol ethers, to which they are by no means limited. The amount of the specific lectin contained in the solvent or diluent is chosen appropriately depending on the agglutination value (which is defined as the final or maximum dilution of serially 2-fold diluted samples), the type of the labeling agent, or the substance to be determined, etc. Usually, the specific lectin is contained in an amount of from about 0.01 to about 100 $\mu$g/ml, preferably from 0.03 to 40 $\mu$g/ml. The above solution of the labeled or unlabeled specific lectin can be diluted further.

The objects of the present invention can be achieved with further advantage by a competitive process or sandwiching process as described below.

(1) The TAG in a body fluid to be determined (hereunder sometimes referred to as the material to be determined) and a given amount of insolubilized TAG or insolubilized TAG-like material are reacted competitively with the specific lectin that has been labeled with a labeling agent (hereunder referred to as labeled specific lectin), and the insolubilized TAG or insolubilized TAG-like material bound to the labeled specific lectin is separated from the unbound labeled specific lectin, and the activity of the labeling agent on either material is measured to determine the TAG level;

(2) The material to be determined and a given amount of TAG or TAG-like material that has been labeled with a labeling agent (hereunder referred to as labeled TAG and labeled TAG-like material, respectively) are reacted competitively with a given amount of the specific lectin or insolubilized specific lectin and the labeled TAG or labeled TAG-like material bound to the specific lectin or insolubilized specific lectin is separated from the unbound labeled TAG or unbound labeled TAG-like material, and the activity of the labeling agent on either material is measured to determine the TAG level;

(3) The material to be determined is reacted with the insolubilized specific lectin to form a complex of TAG and the insolubilized specific lectin, and the complex is reacted with a given amount of the labeled specific lectin, and the complex bound to the labeled specific lectin is separated from the unbound labeled specific lectin, and the activity of the labeling agent on either material is measured to determine the TAG level.

In the present invention, the term "TAG-like material" indicates a sugar derivative having AG or L-fucose terminus; examples thereof include sugars having AG terminus such as sulfated glycopeptide type A of porcine gastric mucous membrane, cytolipins K and R of human erythrocyte membrane, asialo derivative of human blood active substance type A, mucin type A+ of porcine submandibular membrane, asialo $GM_1$ and Follisman antigenic substance or sugar derivatives having L-fucose terminus such as human blood active substance type $Le^a$ and $Le^b$, sulfated glycoprotein type A of porcine gastric mucous membrane, sulfated glycoprotein active substance type H(O) of porcine gastric mucous membrane and human erythrocyte $H_1$ antigen.

The insolubilized TAG, insolubilized TAG-like material and the insolubilized specific lectin can be prepared by chemically or physically reacting TAG, TAG-like material or the specific lectin with an insoluble carrier. As such insoluble carrier, there are illustrated cellulose powder, Sephadex, Sepharose, polystyrene, filter paper, carboxymethyl cellulose, ion-exchange resin, dextran, plastic film, plastic tube, nylon, glass beads, silk, polyamine-methyl vinyl ether-maleic acid copolymer, amino acid copolymer, ethylene-maleic acid copolymer, etc. Insolubilization can be effected by a covalent bond-forming process [i.e., a diazo process, a peptide process (e.g., an acid amide derivative process, a carboxy chloride resin process, a carbodiimide resin process, a maleic anhydride derivative process, an isocyanate derivative process, a cyanogen bromide-activated polysaccharide process, a cellulose carbonate derivative process, a process using a condensing agent, etc.), an alkylating process, a carrier-binding process using a cross-linking agent such as glutaraldehyde, hexamethylene isocyanate, etc., a carrier-binding process according to Ugi reaction, and the like]; an ion-binding process using such carrier as ion-exchange resin; and a physically adsorbing process using porous glass such as glass beads as a carrier. Of these, the cyanogen bromide-activated polysaccharide process and the carrier-binding process using a cross-linking agent of the covalent bond-forming process is preferred. According to the cyanogen bromide-activated polysaccharide process, insolubilized TAG, insolubilized TAG-like material or insolubilized specific lectin can be obtained by reacting TAG, etc., with a 10- to 1,000-fold amount of a cyanogen bromide-activated carrier in a suitable solvent at 0° to 40° C., preferably at 20° to 30° C., for 2 to 4 hours.

The insolubilized TAG, insolubilized TAG-like material and the insolubilized specific lectin can also be prepared by a radiation-induced polymerization process. That is, an aqueous dispersion of a polymerizable monomer containing TAG, TAG-like material or the specific lectin is prepared and irradiated with light or ionizing radiation to polymerize said monomer and form a polymer matrix of TAG, TAG-like material or the specific lectin. Such aqueous dispersion is prepared by dispersing a hydrophobic polymerizable monomer (A) in a 0.1 to 5 wt% aqueous solution of a water-soluble polymer (B), dispersing hydrophilic polymerizable monomer (C) in an aqueous solution, or dispersing a mixture of the hydrophobic polymerizable monomer (A) with a hydrophilic polymerizable monomer (C) in a 3 to 20 wt% aqueous saline solution, or dispersing the hydrophobic polymerizable monomer (A) in an aqueous solution containing 0.01 to 5 wt% of a surfactant (D). When the thus-prepared dispersion is irradiated with light or ionizing radiation, the polymerizable monomer present as a dispersed phase is polymerized to form a polymer matrix of TAG, TAG-like material or the specific lectin. If desired, the matrix may be formed into a sheet or particles by a suitable means.

As the specific examples of the hydrophobic polymerizable monomer (A), there are illustrated glycidyl methacrylate, ethylene glycol dimethacrylate, diethylene glycol dimethacrylate, triethylene glycol dimethacrylate, trimethylolpropane trimethacrylate, polyethylene glycol 200 dimethacrylate, dipropylene glycol dimethacrylate, 1,4-butylene glycol dimethacrylate, 1,6-hexane glycol dimethacrylate, methoxydiethylene glycol dimethacrylate, methyl methacrylate, ethyl methacrylate, butyl methacrylate, and the corresponding acrylates thereof. In general, any water-insoluble monomer that can be polymerized by irradiation with light or radiation can be used.

As the specific examples of the hydrophilic polymerizable monomer (C), there are illustrated 2-hydroxyethyl methacrylate, methoxytetraethylene glycol methacrylate, methoxypolyethylene glycol 400 methacrylate, methoxypolyethylene glycol 1000 methacrylate, polyethylene glycol 400 dimethacrylate, polyethylene glycol 600 dimethacrylate, methacrylic acid, acrylamide, N-vinyl-2-pyrrolidone, etc., and the corresponding acrylates thereof. In general, any water-soluble monomer that can be polymerized by irradiation with light or radiation can be used.

As the specific examples of the water-soluble polymer (B), there are illustrated polyvinyl pyrrolidone, polymethacrylic acid, polyacrylic acid, polyvinyl alcohol, hydroxypropyl cellulose, gum arabic, etc.

As the specific examples of the surfactant (D), there are illustrated sodium laurylsulfate, potassium oleate, sodium oleate, sorbitan monolaurate, sorbitan monostearate, sorbitan monooleate, propylene glycol monolaurate, oleic acid, sodium dodecylbenzenesulfonate. However, any surfactant that can retain in its micellar structure the polymerizable monomer or TAG, TAG-like material or the specific lectin dissolved in the polymerizable monomer can be used.

Radioactive material-labeled TAG, radioactive material-labeled TAG-like material, and radioactive material-labeled specific lectin can be prepared by introducing into TAG, TAG-like material or specific lectin a radioactive iodine atom such as $^{125}I$ or $^{131}I$. Introduction of radioactive iodine is effected by ordinary iodizing processes, for example, an oxidative iodination process using chloramine T [*Nature*, 194, p. 495 (1962); *Biochem. J.*, 89, p. 114 (1963)]. That is, such iodination is conducted in a suitable solvent [e.g., buffer solution of pH 6-8, preferably 0.2M phosphate buffer solution (pH 7)] at about room temperature for 5 to 60 seconds in the presence of chloramine T. Radioactive iodine and chloramine T are preferably used in amounts of 1 to 5 mCi and 10 to 100 nano moles, respectively, per nano mole of tyrosine contained in TAG, TAG-like material or specific lectin. The thus-labeled TAG, TAG-like material or specific lectin is isolated and separated in a conventional manner and stored, if necessary, in the lyophilized form.

Enzyme-labeled TAG, enzyme-labeled TAG-like material, and enzyme-labeled specific lectin can be prepared by a known coupling process [for example, B. F. Erlanger et al., *Acta. Endocrinol. Suppl.*, 168, 206 (1972) and M. H. Karol et al., *Proc. Nat. Acad. Sci. USA*, 57, 713 (1967)]. That is, TAG, TAG-like material or specific lectin is reacted with an enzyme in a buffer solution of pH 4-6 (e.g., 1 mM acetate buffer solution (pH 4.4) at room temperature for 2 to 5 hours in the presence of an oxidizing agent such as $NaIO_4$ followed by reduction with $NaBH_4$ or the like. Enzyme is used in an amount of 1 to 3 moles per mole of TAG or the like. The oxidizing agent is used in an amount of 100 to 300 moles per mole of TAG or the like, and the reducing agent in an amount of 1 to 2 moles.

Fluorescent material-labeled TAG, fluorescent material-labeled TAG-like material, and fluorescent material-labeled specific lectin are prepared by reacting TAG, TAG-like material or specific lectin with a known flurorescent material such as fluorescein isothiocyanate (FITC) or tetramethylrhodamine isothiocyanate (RITC) in water or a physiological saline solution of pH 6-8 at 0° C. to room temperature, preferably at room temperature, for 0.5 to 3 hours (fluorescent antibody process; *Ikagaku Jikkenho Koza*, No. 4, pp. 263-270). The fluorescent material is preferably used in an amount of 1/50 of TAG or the like.

The determining process of the present invention by the competitive process or sandwiching process will be described below.

In the two processes, the reactions are effected in a suitable solvent at 45° C. or lower, preferably 4° to 40° C., more preferably 20° to 40° C. As such solvent, those which do not adversely affect the reaction of TAG or TAG-like material with specific lectin, such as water, physiological saline, and buffer solutions of pH 6 to 7.8 (e.g., 0.1 to 0.3M tris-hydrochloric acid buffer solution (pH about 7.5), 0.1M phosphate buffer solution (pH about 7.4), etc.) are preferred. The reactions are conducted for 5 to 40 hours, preferably 15 to 25 hours.

The resulting TAG (or TAG-like material) bound to the specific lectin can be separated from the unbound specific lectin or unbound TAG (or TAG-like material) by a known method. If the insolubilized TAG (or TAG-like material) or insolubilized specific lectin is used, the solid phase is simply separated from the liquid phase by centrifugation, filtration or decantation. In other cases, chromatography, electrophoresis, salting out, fractionation, dialysis, gel filtration, adsorption or combinations thereof may be used, or a separation process using agar gel, agarose gel or polyacrylamide gel as described in Japanese Patent Application (OPI) No. 151263/80 may be used.

The activity of the labeling agent for the thus-separated product can be measured by a suitable method selected from among the already described techniques depending on the type of the labeling agent. The measured activity can be used to determine the TAG level of the sample.

As has been described above, the present invention achieves advantageous determination of the TAG level of the body fluid. The determined TAG level can be used for diagnosing cancer of any stage, and the inventon is particularly useful for discovering cancer in early stage. Furthermore, the process of the invention determines the glycolinkage so that in comparison with the conventional processes most of which use antibodies to measure the protein moiety ($\alpha_1$-fetoprotein, CEA, etc.), the process can be used for diagnosing a wider range of cancers including malignant lymphadenosis, malignant lymphoma, chorion-epithelioma malignum, liver cancer, gall bladder cancer, pancreatic cancer, lung cancer, bile duct cancer, thyroid gland cancer, multiple myelome, gastric cancer, breast cancer, carcinoma of the colon, rectal cancer, ovarium cancer, mouth cancer, tongue cancer, laryngeal cancer, prostatic cancer, liposarcoma, malignant melanoma, uterine cancer and stomach-primary sarcoma. The process has specificity depending upon the specific lectin used; if the AG-binding lectin is used, the invention is particularly useful in diagnosing cancers derived from undifferentiated cells such as malignant lymphadenosis, malignant lymphoma and chorion-epithelioma malignum. Further, the method for diagnosing cancers using AG-binding lectin or L-fucose-binding lectin according to the present invention is advantageous in that this method shows a considerably decreased cross-reactivity with diseases other than cancers, e.g., hepatic induration, hepatitis, peptic ulcer, diabetes mellitus, colitis, etc., as compared with conventional diagnostic methods for cancers by the determination of $\alpha_1$-fetoprotein, CEA and the like. The conventional diagnostic methods very often give positive results for hepatic diseases, in particular hepatic induration, acute and chronic hepatitis and the like and cause diagnoses of cancers to be confused greatly. On the other hand, the diagnostic method of the present invention shows a low cross-reactivity with hepatic diseases and thus achieves accurate diagnosis of cancers.

In addition, the present invention is capable of determining sugars and sugar derivatives (e.g., glycopeptides, glycoproteins, glycolipids, glycoterpenes and glycosteroids) having the AG or L-fucose terminus.

The present invention is now described in greater detail by reference to the following non-limiting examples.

EXAMPLE 1

(i) Activation of Peroxidase 5 mg of peroxidase (of horseradish origin) was dissolved in 1 ml of a 0.3M sodium hydrogencarbonate aqueous solution. 0.1 ml of a 0.1M fluorodinitrobenzene ethanol solution was added to the resulting solution, to which after gently stirring for 1 hour at room temperature, was added 0.1 ml of a 0.06M $NaIO_4$ solution followed by gently stirring for 30 minutes at room temperature. Further, 1 ml of a 0.16M ethylene glycol was added to the reaction mixture, and the resulting solution was gently stirred at room temperature for 1 hour. Then, the solution was dialyzed against 0.01M carbonic acid-sodium hydrogencarbonate buffer solution (pH 9.5) at 4° C. for one whole day and night.

(ii) Process for Labeling Lectin with Peroxidase (Dolichos Bean Lectin-Peroxidase)

5 mg of Dolichos bean lectin was dissolved in 3 ml of activated peroxidase obtained in (i), and gently stirred at room temperature for 2-3 hours to react. 5 mg of $NaBH_4$ was added thereto and reacted at 4° C. for 3 hours. Thereafter, this solution was dialyzed against a 0.1M tris-hydrochloric acid buffer solution (pH 7.4) for one day and one night, and subjected to Sephadex G 150 gel column chromatography (eluant: 0.1M tris-hydrochloric acid buffer solution; pH 7.4) to conduct gel filtration. Each fraction was measured at $OD_{280}$ and $OD_{403}$ and fractions having the peaks for $OD_{280}$ and $OD_{403}$ were collected.

(iii) Process for Labeling Lectin with Peroxidase (Lotus tetragonolobus Lectin-Peroxidase)

5 mg of Lotus tetragonolobus lectin was dissolved in 3 ml of the activated peroxidase obtained in (i), and the solution was gently stirred at room temperature for 2 to 3 hours. 5 mg of $NaBH_4$ was added to the solution and held at 4° C. for 3 hours. The reaction liquor was dialyzed against a 0.1M tris-hydrochloric acid buffer solution (pH: 7.4) for one whole day and night, and subjected to gel filtration by Sephadex G 150 gel column chromatography (eluant: 0.1M tris-hydrochlolic acid buffer solution, pH: 7.4). Each fraction was measured at $OD_{280}$ and $OD_{403}$ and fractions having the peaks for $OD_{280}$ and $OD_{403}$ were collected.

(iv) Process for Preparing Insolubilized Lectin 15 g of CNBr-activated agarose was suspended in 3 liters of 0.001N hydrochloric acid and, after allowing to stand for 30 minutes, washed with 1 liter of 0.1M sodium hydrogencarbonate (pH 8.5) on a glass filter. Thus, there was obtained a total of about 50 ml of activated agarose. This was suspended in 200 ml of 0.1M sodium hydrogencarbonate (pH 8.5), and 5 ml of a 0.01M phosphate buffer solution (pH 7.7) containing 50 mg of Dolichos bean lectin was added thereto followed by reacting at room temperature for 2 hours with stirring at times. After completion of the reaction, the reaction solution was washed on a glass filter, and the reaction product was added to 200 ml of a 1M monoethanolamine solution (pH 8.5) and reacted for 2 hours at room temperature. Thereafter, the reaction product was washed on a glass filter. In the above procedures, washing was conducted using 1 liter of a 0.1M acetic acid buffer solution (containing 0.5M NaCl) and 1 liter of a 0.1M boric acid buffer solution (containing 0.5M NaCl) alternately three times.

(v) Process for Preparing Insolubilized Lectin 15 g of CNBr-activated agarose was suspended in 3 liters of 0.001N hydrochloric acid and, after allowing to stand for 30 minutes, washed with 1 liter of 0.1M sodium hydrogencarbonate (pH: 8.5) on a glass filter. Thus, there was obtained a total of about 50 ml of activated agarose. This was suspended in 200 ml of 0.1M sodium hydrogencarbonate (pH: 8.5) and 5 ml of a 0.01M phosphate buffer solution (pH 7.7) containing 50 mg of Lotus tetragonolobus lectin was added thereto followed by reacting at room temperature for 2 hours with occasional stirring. After completion of the reaction, the reaction solution was washed on a glass filter, and the reaction was added to 200 ml of a 1M monoethanolamine solution (pH: 8.5) and reacted for 2 hours at room temperature. Thereafter, the reaction product was washed on a glass filter. In the above procedures, washing was conducted using 1 liter of a 0.1M acetic acid buffer solution (containing 0.5M NaCl) and 1 liter of a 0.1M boric acid buffer solution (containing 0.5M NaCl) alternately three times.

(vi) Process for Preparing TAG-Like Material

Sulfated glycoprotein (1 g) of porcine gastric mucosa (hereinafter abbreviated as PGM) was suspended in 100 ml of a 0.05M phosphate buffer solution (pH 7.0), and a 1N NaOH aqueous solution was dropwise added thereto to adjust the pH to 11. After stirring for 30 minutes at room temperature, the mixture was centrifuged for 10 minutes at 3,000 rpm, and the supernatant was adjusted to pH 7.0 with 1N HCl followed by again centrifuging for 10 minutes at 3,000 rpm. The supernatant was dialyzed against 10 liters of a 0.1M phosphate buffer solution (pH 7.0) overnight to obtain purified TAG-like material (pure PGM).

(vii) Process for Preparing Labeled TAG-Like Material (a) Labeling with an enzyme (PGM-Peroxidase)

4 mg of peroxidase of horseradish origin (HRPO) (0.1 $\mu$M) was dissolved in 1 ml of distilled water. To this was added 0.2 ml of 0.1M NaIO$_4$ and, after stirring at room temperature for 20 minutes, the solution was dialyzed against 1 mM acetic acid buffer solution (pH 4.4) for one day and one night to remove unreacted NaIO$_4$. To this dialyzed reaction solution was added about 60 $\mu$l of a 0.2M hydrogencarbonate buffer solution (pH 9.5) to adjust the pH of the solution to 9.0. Then, to this solution was immediately added 0.6 ml of PGM (10 mg/ml) dissolved in a 0.01M hydrogencarbonate buffer solution (pH 9.5), mixed for 2 hours at room temperature, and 0.1 ml of a 4 mg/ml of NaBH$_4$ solution in distilled water was added thereto followed by allowing to stand at 4° C. for 2 hours. Further, this solution was dialyzed against a 0.01M phosphate buffer solution (pH 7.2) for one whole day and night, and purified using Sephadex G-200 (1.5×150 cm) to obtain pure PGM-peroxidase (PGM-POX). The gel effluent was collected by 5 ml portions the absorption of which was measured at OD$_{280}$ and OD$_{403}$.

(b) Labeling with Isotope ($^{125}$I-PGM):

PGM was labeled with $^{125}$I according to an oxidative iodination process using chloramine T.

10 $\mu$g of PGM was dissolved in 50 $\mu$l of a 0.2M phosphate buffer solution (pH 7.0), and 10 $\mu$l of 1 mCi of Na$^{125}$I (carrier-free; N.E.N.) and 50 $\mu$g/100 $\mu$l of chloramine T solution in a 0.2M phosphate buffer solution were added thereto and, after mixing at room temperature for 30 seconds, 100 $\mu$g/100 $\mu$l of Na$_2$S$_2$O$_5$ solution in a 0.2M phosphate buffer solution was added thereto. Then, 1 mg of Na$^{127}$I was added thereto and mixed. The thus-obtained $^{125}$I-PGM was purified on Sephadex G-50 (1×30 cm). The thus-prepared $^{125}$I-PGM had a radioactivity of about 1-2 $\mu$Ci/$\mu$g.

Figure 1:
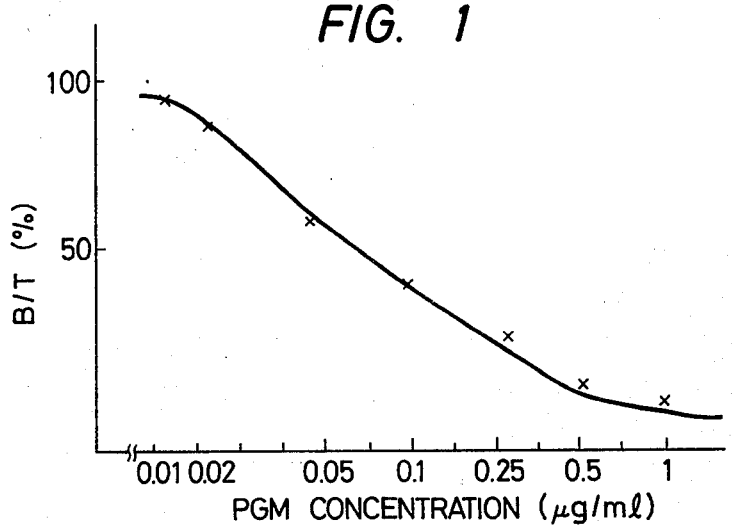

(viii) Determining Process 0.1 ml of $^{125}$I-PGM (100 ng 0.17 $\mu$Ci corresponding to about 2.4×10$^5$ cpm) obtained in (vii), 0.1 ml of the pure standard PGM (0.1 $\mu$g/ml, 0.2 $\mu$g/ml, 0.5 $\mu$g/ml, 1 $\mu$g/ml, 2.5 $\mu$g/ml, 5 $\mu$g/ml, 10 $\mu$g/ml) obtained in (vi), 0.1 ml of Dolichos bean lectin (10 $\mu$g/ml), and 0.2 ml of a 0.05M phosphoric acid buffer solution (0.15M NaCl; 0.1% BSA: 0.02% NaN$_3$) were mixed in a 10×75 mm glass tube, and incubated at 25° C. for 1 hour. After completion of the reaction, 0.1 ml of anti-DBA rabbit serum (made by E.Y. Laboratory; 10-times diluted solution) was added to the $^{125}$I-PGM bound to DBA and $^{125}$I-PGM unbound to DBA and, after incubating at 25° C. for 1 hour, the reaction solution was centrifuged at 4° C. for 30 minutes at 3,000 rpm. The radioactivity of the precipitate ($^{125}$I-PGM bound to DBA) was counted to prepare a standard curve (FIG. 1). As is clear from the results thus-obtained, % Bound (B/T) was usually 20 to 25% and 50% inhibition was obtained at a concentration of 0.06 $\mu$g/ml.

Figure 2:
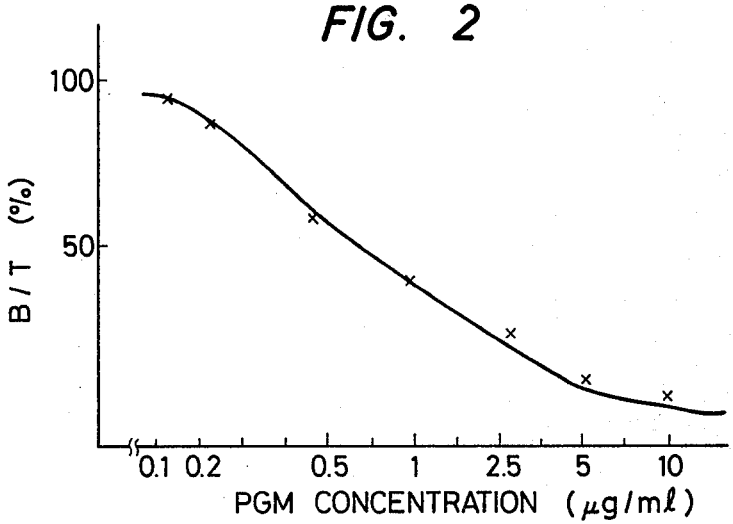

(ix) Determining Process 0.1 ml of $^{125}$I-PGM (100 ng 0.17 $\mu$Ci corresponding to about 2.4×10$^5$ cpm) obtained in (vii), 0.1 ml of the pure standard PGM (0.1 $\mu$g/ml, 0.2 $\mu$g/ml, 0.5 $\mu$g/ml, 1 $\mu$g/ml, 2.5 $\mu$g/ml, 5 $\mu$g/ml, 10 $\mu$g/ml) obtained in (vi), 0.1 ml of Lotus tetragonolobus lectin (10 $\mu$g/ml), and 0.2 ml of a 0.05M phosphoric acid buffer solution (0.15M NaCl; 0.1% BSA: 0.02% NaN$_3$) were mixed in a 10×75 mm glass tube, and incubated at 25° C. for 1 hour. After completion of the reaction, 0.1 ml of anti-Lotus tetragonolobus lectin rabbit serum (made by E.Y. Laboratory; 10-times diluted solution) was added to the $^{125}$I-PGM bound to Lotus tetragonolobus lectin and $^{125}$I-PGM unbound to Lotus tetragonolobus lectin and, after incubating at 25° C. for 1 hour, the reaction solution was centrifuged at 4° C. for 30 minutes at 3,000 rpm. The radioactivity of the precipitate ($^{125}$I-PGM bound to Lotus tetragonolobus lectin) was counted to prepare a standard curve (FIG. 2). As is clear from the results thus-obtained, % Bound (B/T) was usually 20 to 25% and 50% inhibition was obtained at a concentration of 0.6 $\mu$g/ml.

(x) Preparation of Insolubilized TAG-Like Material (Preparation of PGM-Insolubilized Sheet)

An excess amount of PGM was added to 100 ml of a 0.01M phosphate buffer solution (pH 7.0) to prepare a suspension. A 0.01N NaOH solution was added thereto to adjust the pH of the suspension to about 11, followed by centrifuging at 3,000 rpm for 20 minutes to recover the supernatant. To this supernatant was dropwise added 0.03N HCl to adjust the pH to 7.0, and centrifugation was again conducted at 3,000 rpm for 20 minutes. The supernatant was dialyzed against a 0.01M phosphate buffer solution (pH 7.0) to prepare a PGM solution. As to the sugar content and protein content of the solution, hexose content was measured to be 5 to 7 mg/ml according to a phenol-sulfuric acid method using glucose as a standard, and protein content was measured to be 1 to 2 mg/ml using BSA as a standard. The PGM solution was subjected to the following radiation-induced polymerization.

The radiation-induced polymerization was conducted as follows. Hydroxyethyl methacrylate (HEMA) (used as a monomer) was mixed with the above-described PGM solution in a mixing ratio of 33:67, and the resulting mixture was placed in a 1 cm×15 to 20 cm glass tube and rapidly lyophilized to $-70°$ C. or lower. Subsequently, it was irradiated with $1\times10^6$ rad gamma rays to polymerize the monomer. The polymer rod was sliced into discs each having a thickness of 10 μm.

(xi) Preparation of Insolubilized TAG-Like Material 15 g (dry weight) of CNBr-activated Sepharose 4B (made by Pharmacia AB) was suspended in 3 liters of 0.001N hydrochloric acid and, after allowing to stand for 30 minutes, washed with 1 liter of 0.1M sodium hydrogencarbonate (pH 8.5) on a glass filter to obtain about 50 ml of activated Sepharose. This was suspended in 200 ml of 0.1M sodium hydrogencarbonate (pH 8.5), and 5 ml of a 0.01M phosphate buffer solution (pH 7.7) containing 50 mg of PGM was added thereto followed by reacting at room temperature for 2 hours with stirring at times.

After completion of the reaction, the reaction solution was meshed on a glass filter, and the reaction product was added to 200 ml of a 1M monoethanolamine solution (pH 8.5) followed by reacting at room temperature for 2 hours. Then, the reaction solution was washed on a glass filter with 1 liter of a 0.1M acetic acid buffer solution (containing 0.5M NaCl) and 1 liter of a 0.1M boric acid buffer solution (containing 0.5M NaCl) alternately three times.

(xii) Process for Preparation of Insolubilized TAG-Like Material (Preparation of PGM-Beads)

10,000 polystyrene beads having a diameter of 6.4 mm manufactured by Precision Plastic Co., Ltd., U.S.A. were washed with a diluted solution of synthetic soap (mamalemon ®, manufactured by Lion Co., Ltd.) at a concentration of 1.5 ml/1 l of distilled water and then with distilled water. Further, after dipping them in 0.5M NaOH aqueous solution for 3 days the beads were washed thoroughly until the pH of the washing became about 6. The thus-washed 10,000 beads were added in 2.5 liters of 35 (w/v) % PGM solution in 50 mM acetic acid buffer adjusted to pH 4.5 with 10N NaOH, rotated at about 10 rpm for 24 hours, filtered and washed with 8 liters of distilled water four times. Then, the beads were added to 2.5 liters of glutaraldehyde solution of final concentration 1 v/v % in 50 mM sodium phosphate buffer (pH 7), rotated at 10 rpm for 2 hours, filtered and washed with distilled water in the same manner as above. The thus-treated 10,000 beads were added to 2.5 liters of 1M glycine solution in 50 mM sodium phosphate buffer (pH 7.0), rotated at 10 rpm for 2 hours, filtered and washed with distilled water in the same manner as above followed by drying at 37° C. overnight to obtain PGM-beads. The surface area of beads was determined according to Orcinol-H$_2$SO$_4$ method (M. Schönenberger, et al., Z. Physiol. Chem., 309, 145 (1957)) and the result obtained is 2.7±0.2 μg PGM/bead.

EXAMPLE 2

(i) Preparation of Test Samples

Blood samples each measuring 5 ml were drawn from patients with various cancers, patients with non-malignant diseases and healthy persons with heparin (500 units)-treated syringes, and the samples were centrifuged at 2,000 rpm for 10 minutes, and test samples were prepared from the supernatant.

(ii) Measurement

To 0.1 ml of each of the test samples prepared in (i), an equivolume of 10 μg/ml of Dolichos bean lectin-peroxidase in 0.2 ml of 0.15M phosphate buffer solution and one PGM-insolubilized sheet were added, and the mixture was well stirred and left to stand at 20°–37° C. for 24 hours. After thoroughly washing the PGM-insolubilized sheet in the reaction liquor, the activity of the Dolichos bean lectin-peroxidase bound to the sheet was measured from OD$_{492}$ by the enzymatic activity determination process using H$_2$O$_2$ as a substrate and orthophenylenediamine as a coloring agent. A calibration curve was obtained by replacing the test samples with a standard material (PGM) of various concentrations, and is shown in FIGS. 3 and 3', wherein the values of TAG-D are indicated as a hexose-reduced level of PGM and N-acetylgalactosamine-reduced level of PGM, respectively.

(iii) Results

Figure 3:
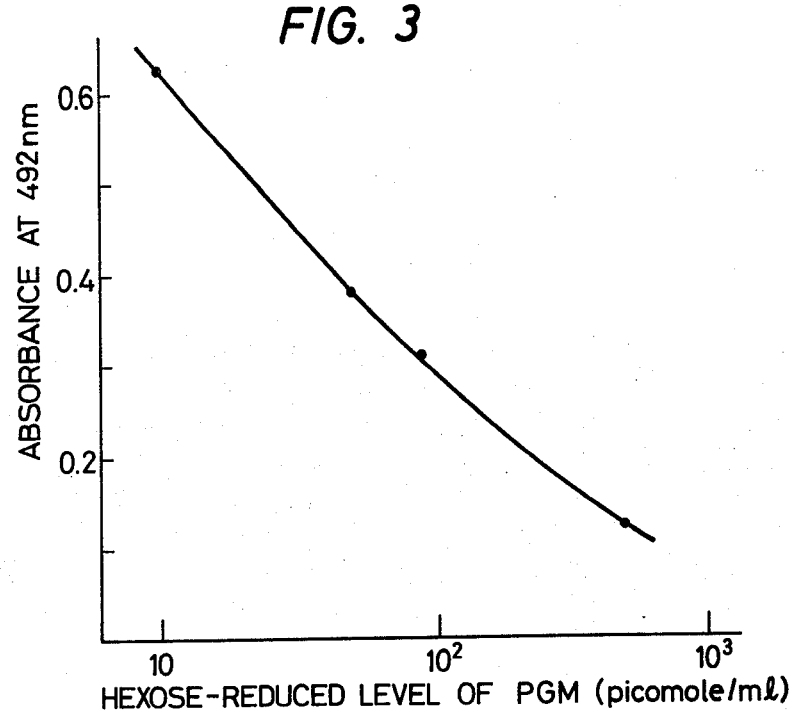
Figure 3:
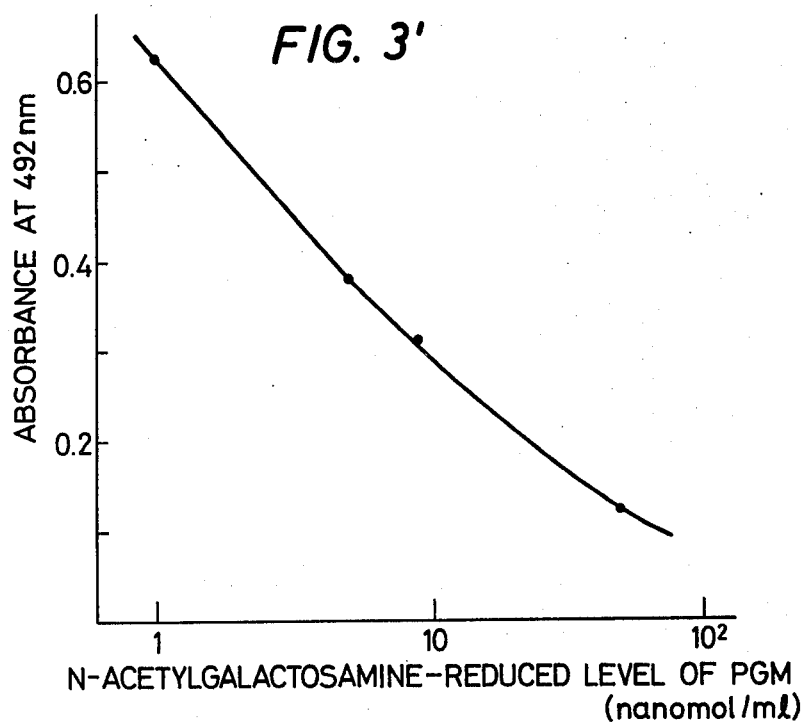

The results were obtained using a standard curve shown in FIG. 3.

Figure 4:
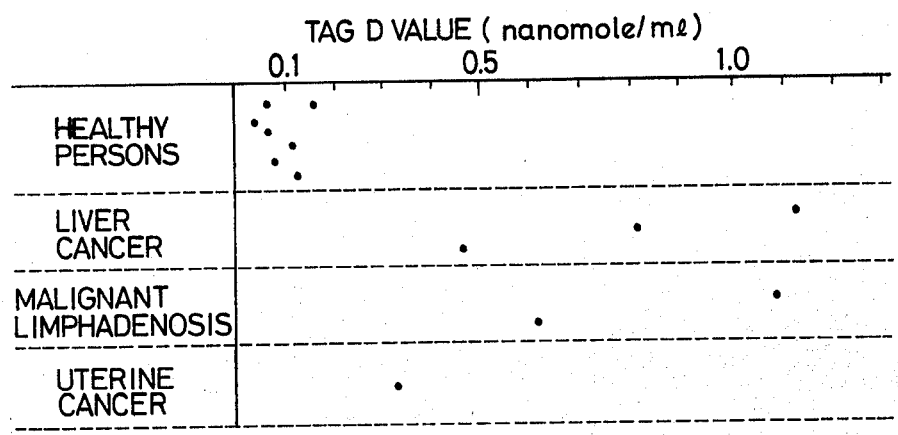
FIG. 4 is a graph showing the level of TAG in healthy persons and patients with various cancers determined by using the process of the present invention using the competitive reaction process of Example 2(iii).

As shown in FIG. 4, all healthy persons had a TAG-D value of about 0.1 n moles/ml.

EXAMPLE 3

(i) Preparation of Agarose Gel

An agarose (product of Iwai Kagaku Co., Ltd.) was suspended in 0.01M tris-hydrochloric acid buffer solution (pH: 7.5) to give a concentration of 1 w/w %. The suspension was heated at 70°–80° C. to form a solution, to which 0.01 w/v % of thimerosal was added. The solution was distributed among test tubes by 1 ml and left to stand at room temperature to prepare agarose gels having a concentration of 1 w/w %.

(ii) Measurement

Two test samples (200 μl each) were put in two test tubes, into which 50 μl of peroxidase-labeled Dolichos bean lectin (3.5 μg/ml of lectin in 0.1 M tris-hydrochloric acid buffer solution having a pH of about 7.5) was added. Each mixture was stirred lightly and left to stand at 20°–30° C. for one hour.

Figure 5:
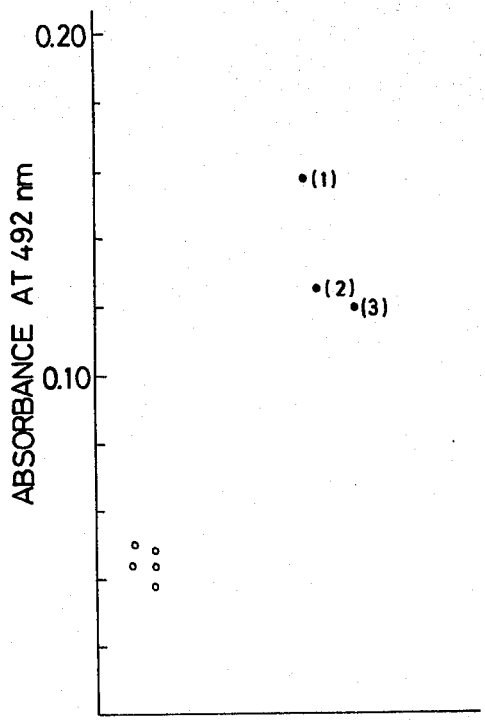
FIG. 5 is a graph showing the level of TAG in healthy persons and patients with various cancers according to Example 3(ii).

To one sample (Sample A) was added 250 μl of 8 w/V % solution of polyethylene glycol (m.w.=6,000) in 0.1M tris-hydrochloric acid buffer solution, and to the other sample (Sample B), 250 μl of 0.1M tris-hydrochloric acid buffer solution was added, and each mixture was stirred lightly. Both samples were left to stand at 20°–30° C. for 30–60 minutes and centrifuged with a swing rotor at 1,000 G for 40 to 60 minutes. The supernatant (50 μl) was decanted into 2 ml of physiological saline and the mixture was thoroughly stirred. To each mixture, 500 μl of a solution of peroxidase substrate (hereunder referred to as the substrate liquor) was added, and the mixture was left to stand in a dark room at 20°–30° C. for 30 minutes. The substrate liquor was prepared by adding orthophenylenediamine and aqueous hydrogen peroxide to 0.1M citrate-phosphate buffer solution to give the respective final concentrations of 6% and 0.1%. The substrate liquor is preferably held at 4° C. until use. The enzymatic reaction was stopped by adding 1 ml of 2N hydrochloric acid. The color change was evaluated by measuring the absorbance at 492 nm with a spectrophotometer. The value (c) obtained by subtracting the absorbance (a) of Sample A from the absorbance (b) of Sample B was plotted as the amount of TAG-bound lectin. The result is shown in FIG. 5, in which the circle indicates the healthy persons, the numerals (1) and (2) indicate the patients with liver cancer and (3) indicates the patients with malignant lymphadenosis. The samples having a higher value (c) than those from the healthy persons mean a higher TAG level in plasma, and suggest that cancerous cells were produced in the hosts.

(iii) Sandwiching Process

200 μg of DBA-agarose was added to 100 μl of a 0.05M phosphate buffer solution (pH 7.0) containing dissolved therein 1 to 10 μg/ml of PGM, and incubation was conducted at 25° C. for 1 hour under stirring. After washing the reaction solution three times with a 0.05M phosphate buffer solution (pH 7.0), 6 μg of DBA labeled with peroxidase obtained in Example 1-(ii) and 100 μl of a 0.05M phosphate buffer solution (pH 7.0) were added thereto followed by incubating at 25° C. for 1 hour under stirring. After centrifuging at 3,000 rpm for 10 minutes, the precipitate was recovered and washed three times with a 0.05M phosphate buffer solution (pH 7.0)

60 mg of orthophenylenediamine was dissolved in 20 ml of 0.2M Mcllevein buffer (pH 5.8) and $H_2O_2$ was added to the resulting solution at a final concentration of 0.02 v/v %, and the mixture was stirred to form a coloring agent.

Figure 6:
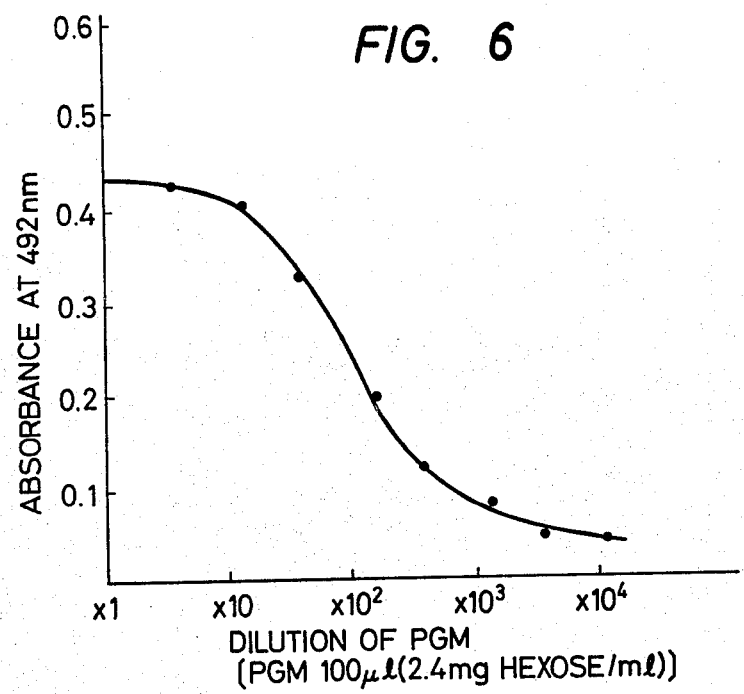
FIG. 6 is a graph showing a calibration curve of another embodiment of the process of the present invention using a sandwich process of Example3(iii).

In a test tube were placed 2 ml of physiological saline solution and 500 μl of the coloring agent as well as the washed bead followed by incubating at room temperature for 30 minutes. Then, the enzymatic reaction was stopped with 1 ml of 3N HCl. The absorbance was measured at 492 nm. The results thus-obtained are shown in FIG. 6.

(iv) Competitive Process

100 μl of a sample (test sample obtained in Example 2-(i)) was placed in a test tube to which 500 μl of 0.3M tris-HCl buffer (pH 7.4) containing therein a final 0.22 w/v % of gelatin, 5 mM $CaCl_2$ and 5 mM $MgCl_2$ was added. One PGM-bead (insolubilized TAG-like material prepared in Example 1-(xii)) and 100 μl of lectin-peroxidase (the lyophilized labeled DBA prepared in Example 1-(ii) at a concentration of 1 mg/l of the above-described tris-HCl buffer) was added to the sample and after stirring the mixture was incubated for 48 hours at 4° C. The reaction mixture was removed using an aspirator and the bead was washed with 2 ml of physiological saline solution followed by removing the washings using an aspirator. This washing operation was repeated three times.

60 mg of orthophenylenediamine was dissolved in 20 ml of 0.2M Mcllevein buffer (pH 5.8) and $H_2O_2$ was added to the resulting solution at a final concentration of 0.02 v/v %, and the mixture was stirred to form a coloring agent.

Figure 8A:
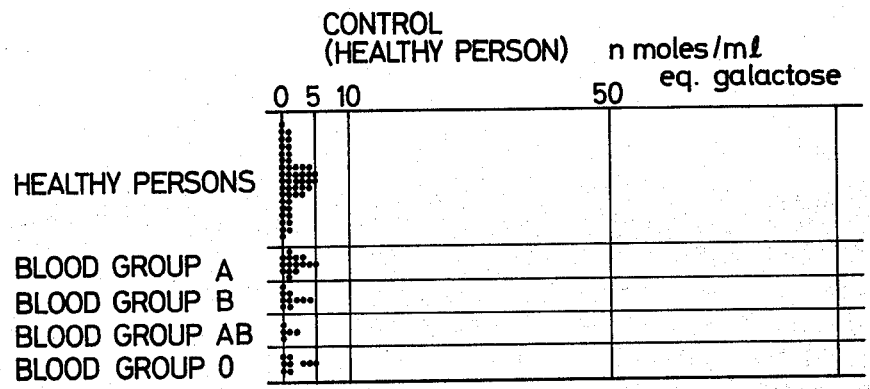
Figure 8B:
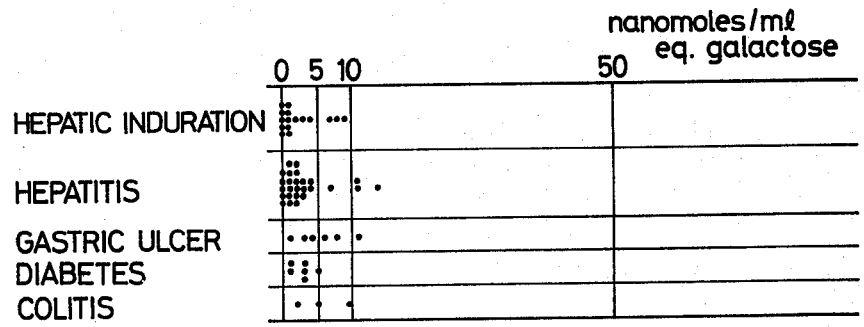
Figure 8C:
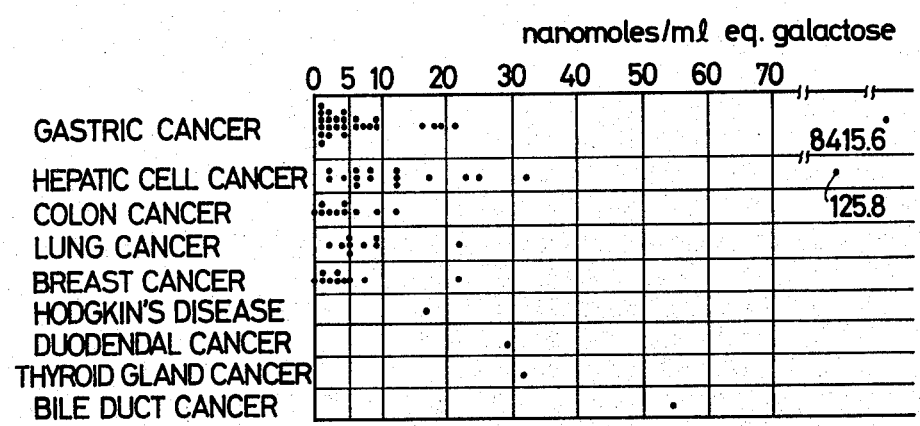

In a test tube were placed 2 ml of physiological saline solution and 500 μl of the coloring agent as well as the washed bead followed by incubating at room temperature for 30 minutes. Then, the enzymatic reaction was stopped with 1 ml of 3N HCl. The optical density of the reaction mixture was measured at 492 nm. At the same time, absorbance was measured in the same manner except for changing the sample to various concentrations of a standard material (PGM) to prepare a calibration curve (FIG. 7). Further, TAG in the test samples obtained in Example 2-(i) was determined using the calibration curve. The results obtained are shown in FIGS. 8(a), 8(b) and 8(c).

EXAMPLE 4

(i) Competitive Process

A slice of disc (insolubilized TAG-like material prepared in Example 1-(x)) was placed in 50 μl of Lotus tetragonolobus lectin-bound peroxidase (labeled lectin prepared in Example 1-(iii)) and 200 μl of the sample (PGM of various concentrations), and incubated at 25° C. for 20 hours. Then, the disc was washed with PBS and placed in 2.0 ml of a saline aqueous solution, and 0.5 ml of a peroxidase material was added thereto followed by incubating at 25° C. for 1 hour. Then 1.0 ml of 3N hydrochloric acid was added thereto, and the absorbance was measured at 492 nm. At the same time, the absorbance was measured in the same manner except for changing the sample to various concentrations of a standard material (PGM) to prepare a calibration curve (FIGS. 9 and 9', wherein the values of TAG are indicated as a hexose-reduced level of PGM and L-fucose-reduced level of PGM, respectively).

(ii) Sandwiching Process

200 μg of Lotus tetragonolobus lectin-agarose was added to 100 μl of a 0.05M phosphate buffer solution (pH: 7.0) having dissolved therein 1 to 10 μg/ml of PGM, and incubation was conducted at 25° C. for 1 hour under stirring. After washing the reaction solution three times with a 0.05M phosphate buffer solution (pH: 7.0), 6 μg of peroxidase-labeled Lotus tetragonolobus obtained in Example 1-(iii) and 100 μl of a 0.05M phosphate buffer solution (pH: 7.0) were added thereto, followed by incubation at 25° C. for 1 hour under stirring. After centrifugation at 3,000 rpm for 10 minutes, the precipitate was recovered and washed three times with a 0.05M phosphate buffer solution (pH: 7.0).

60 mg of orthophenylenediamine was dissolved in 20 ml of 0.2M Mcllevein buffer (pH 5.8) and $H_2O_2$ was added to the resulting solution at a final concentration of 0.02 v/v %, and the mixture was stirred to form a coloring agent.

In a test tube were placed 2 ml of physiological saline solution and 500 μl of the coloring agent as well as the washed bead followed by incubating at room temperature for 30 minutes. Then, the enzymatic reaction was stopped with 1 ml of 3N HCl. The absorbance was measured at 492 nm. At the same time, the absorbance was measured in the same manner except for changing the sample to various concentrations of a standard material (PGM) to prepare a calibration curve shown in FIG. 10.

(iii) Determination

To 0.1 ml of each of the test samples prepared in Example 2-(i), an equivolume of 10 μg/ml of Lotus tetragonolobus lectin-peroxidase in 0.2 ml of 0.15M phosphate buffer solution and the one PGM-insolubilized sheet were added, and the mixture was well stirred and left to stand at 20°–37° C. for 24 hours. After thoroughly washing the PGM-insolubilized sheet in the reaction liquor, the activity of the Lotus tetragonolobus lectin-peroxidase bound to the sheet was measured from $OD_{492}$ by the enzymatic activity determination process using $H_2O_2$ as a substrate and orthophenylenediamine as a coloring agent. A calibration curve was obtained by replacing the test samples with a standard material (PGM) of various concentrations, and is shown in FIG. 11 wherein the values of TAG-D are indicated as a hexose-reduced PGM level.

Results

As shown in FIG. 11, all healthy persons had a TAG-D value of less than 3 nM/ml.

(iv) Determination

Two of the test samples (200 μl each) that were prepared in Example 2-(i) were put in two test tubes, into which 50 μl of the peroxidase-labeled Lotus tetragonolobus lectin (3.5 μg/ml of lectin in 0.1M tris-hydrochloric acid buffer solution having a pH of about 7.5) prepared in Example 1-(iii) was added. Each mixture was stirred lightly and left to stand at 20°–30° C. for one hour. To one sample (Sample A) was added 250 μl of 8 w/v % solution of polyethylene glycol (m.w.=6,000) in 0.1M tris-hydrochloric acid buffer solution, and to the other sample (Sample B), 250 μl of 0.1M tris-hydrochloric acid buffer solution was added, and each mixture was stirred lightly. Both samples were left to stand at 20°–30° C. for 30 to 60 minutes and centrifuged with a swing rotor at 1,000 G for 40 to 60 minutes. The supernatant (50 μl) was decanted into 2 ml of physiological saline and the mixture was thoroughly stirred. To each mixture, 500 μl of a solution of peroxidase substrate (hereunder referred to as the substrate liquor) was added, and the mixture was left to stand in a dark room at 20° to 30° C. for 30 minutes. The substrate liquor was prepared by adding orthophenylenediamine and aqueous hydrogen peroxide to 0.1M citrate buffer solution to give the respective final concentrations of 6% and 0.1%. The substrate liquor is preferably held at 4° C. until use. The enzymatic reaction was stopped by adding 1 ml of 2N hydrochloric acid. The color change was evaluated by measuring the absorbance at 492 nm with a spectrophotometer. The value (c) that was obtained by substracting the absorbance (a) of Sample A from the absorbance (b) of Sample B was plotted as the amount of TAG-bound lectin. The result is shown in FIG. 12, in which the circle indicates the healthy persons, the numerals (1) and (2) indicate the patients with gastric cancer, and (3) indicates the patients with breast cancer. The samples having a higher value (c) than those from the healthy persons mean a higher TAG level in plasma, and suggest that cancerous cells were produced in the hosts.

(v) Competitive Process

100 μl of a sample (test sample obtained in Example 2-(i)) was placed in a test tube to which 500 μl of 0.3M tris-HCl buffer (ph 7.4) containing therein a final 0.22 w/v % of gelatin, 5 mM $CaCl_2$ and 5 mM $MgCl_2$ was added. One PGM-bead (insolubilized TAG-like material prepared in Example 1-(xii)) and 100 μl of lactin-peroxidase (the lyophilized labelled DBA prepared in Example 1-(iii) at a concentration of 1 mg/l of the above-described tris-HCl buffer) were added to the sample and after stirring the mixture was incubated for 48 hours at 4° C. The reaction mixture was removed using an aspirator and the bead was washed with 2 ml of physiological saline solution followed by removing the washings using an aspirator. This washing operation was repeated three times.

60 mg of orthophenylenediamine was dissolved in 20 ml of 0.2M Mcllevein buffer (ph 5.8) and $H_2O_2$ was added to the resulting solution at a final concentration of 0.02 v/v %, and the mixture was stirred to form a coloring agent.

In a test tube were placed 2 ml of physiological saline solution and 500 μl of the coloring agent as well as the washed bead followed by incubating at room temperature for 30 minutes. Then, the enzymatic reaction was stopped with 1 ml of 3N HCl. The optical density of the reaction mixture was measured at 492 nm. At the same time, absorbance was measured in the same manner except for changing the sample to various concentrations of a standard material (PGM) to prepare a calibration curve (FIG. 13). Further, TAG in the test samples obtained in Example 2-(i) was determined using the calibration curve. The results obtained are shown in FIG. 14.

While the invention has been described in detail and with reference to specific embodiments thereof, it will be apparent to one skilled in the art that various changes and modifications can be made therein without departing from the spirit and scope thereof.

What is claimed is:

1. A process for determining the level of tumor-associated glycolinkage (TAG) in a sample of body fluid comprising reacting the TAG in a sample of body fluid with an N-acetyl-D-galactosamine (AG)-binding lectin or L-fucose-binding lectin to form a TAG-lectin complex and measuring the amount of the TAG-lectin complex or of unreacted lectin.

2. The process as claimed in claim 1, wherein said lectin is an AG-binding lectin, and said body fluid is blood, tissue fluid, lymph, hydrothorax, ascites, amniotic fluid, gastric juice, urine, pancreatic juice, cerebrospinal fluid or saliva.

3. The process as claimed in claim 1, wherein said lectin is L-fucose binding lectin, and said body fluid is blood, tissue fluid, lymph, hydrothorax, ascites, amniotic fluid, gastric juice, urine, pancreatic juice, cerebrospinal fluid or saliva.

4. The process as claimed in claim 2, wherein the reaction between the TAG and the lectin is carried out by competitively reacting the body fluid TAG to be measured and a definite quantity of an insolubilized TAG or insolubilized sugar derivative having an AG terminus with a definite quantity of labelled lectin, separating the insolubilized TAG or insolubilized sugar derivative having an AG terminus bound to labelled lectin and unbound lectin from each other, and measuring the labelling agent activity of either of them.

5. The process as claimed in claim 2, wherein the reaction between the TAG and the lectin is carried out by competitively reacting body fluid TAG to be measured and a definite quantity of labelled TAG or labelled sugar derivative having an AG terminus with a definite quantity of lectin or insolubilized lectin, separating the labelled TAG or sugar derivative having an AG terminus bound to lectin or insolubilized lectin and unbound labelled TAG or labelled sugar derivative having an AG terminus from each other, and measuring the labelling agent activity of either of them.

6. The process as claimed in claim 2, wherein the reaction between the TAG and the lectin is carried out by reacting the body fluid TAG to be measured with an insolubilized lectin to form a TAG-insolubilized lectin complex, reacting this complex with a definite quantity of labelled lectin, separating the complex bound to the labelled lectin and unbound labelled lectin from each other, and measuring the labelling agent activity of either of them.

7. The method of claim 4, 5, 6 or 2 which further comprises separating TAG from said body fluid sample and reacting the separated TAG with said lectin.

8. A process as claimed in claim 4 or 6 wherein said labelled lectin is lectin labelled with an enzyme selected from the group consisting of alkaline phosphatase $\beta$-galactosidase and hemeoctapeptide.

9. The process as claimed in claim 4 or 6 wherein said labelled lectin is a lectin labelled with a fluorescent substance selected from the group consisting of fluorescein, fluorescein isothiocyanate, rhodamine and dansyl chloride.

10. The process as claimed in claim 4 or 6 wherein said labelled lectin is lectin labelled with a radioactive substance selected from the group consisting of radioactive iodine and tritium.

11. The process as claimed in claim 2, wherein said lectin is a lectin selected from the group consisting of Dolichos bean lectin, braid orange lectin, Helix pomatia lectin, lima-bean lectin, Soybean lectin and Bauhinia bean lectin.

12. The process as claimed in claim 4, wherein said TAG in blood serum or blood plasma and an insolubilized porcine gastric mucous membrane (PGM), insolubilized by radiation-induced polymerization with a hydroxyethyl methacrylate (HEMA) or polystyrene bead, are competitively reacted with a peroxidase labelled DBA.

13. The process as claimed in claim 4 or 5, wherein said sugar derivative having an AG terminus is selected from the group consisting of sulfate glycopeptide type A of porcine gastric mucous membrane, cytolipins K and R of human erythrocyte membrane, asialo derivative of human blood active substance type A, mucin type A+ of porcine submandibular membrane, asialo GM$_1$ and Forssman antigenic substance.

14. The process as claimed in claim 5, wherein said TAG in blood serum or blood plasma and $^{125}$I-PGM are competitively reacted with DBA.

15. The process as claimed in claim 5, wherein said body fluid is blood serum or blood plasma and said AG-binding lectin is a Dolichos bean lectin (DBA) labelled with a peroxidase.

16. The process as claimed in claim 6, wherein said TAG in blood serum or blood plasma is reacted with DBA-agarose and the resulting complex is further reacted with a peroxidase labelled DBA.

17. The process as claimed in claim 3, wherein said lectin is Lotus tetragonolobus lectin (LTL) or Ulex europeus lectin.

18. The process as claimed in claim 3, wherein the reaction between the TAG and the lectin is carried out by competititely reacting the body fluid TAG to be measured and a definite quantity of an insolubilized TAG or insolubilized sugar derivative having an L-fucose terminus with a definite quantity of labelled lectin, separating the insolubilized TAG or insolubilized sugar derivative having an L-fucose terminus bound to labelled lectin and unbound lectin from each other, and measuring the labelling agent activity of either of them.

19. The process as claimed in claim 3, wherein reaction between the TAG as the lectin is carried out by competitively reacting body fluid TAG to be measured and a definite quantity of labelled TAG or labelled sugar derivative having an L-fucose terminus with a definite quantity of lectin or insolubilized lectin, separating the labelled TAG or labelled sugar derivative having an L-fucose terminus bound to lectin or insolubilized lectin and unbound labelled TAG or labelled sugar derivative having an L-fucose terminus from each other, and measuring the labelling agent activity of either of them.

20. The process as claimed in claim 3, wherein the reaction between the TAG and the lectin is carried out by reacting the body fluid TAG to be measured with an insolubilized lectin to form a TAG-insolubilized lectin complex, reacting this complex with a definite quantity of labelled lectin, separating the complex bound to the labelled lectin and unbound labelled lectin from each other, and measuring the labelling agent activity of either of them.

21. The process as claimed in claim 3, wherein said body fluid is blood serum or blood plasma, and said L-fucose binding lectin is peroxidase labelled LTL.

22. The process as claimed in claim 18 or 19, wherein said sugar derivative having an L-fucose terminus is a sugar derivative selected from the group consisting of human blood active substance type Le$^a$ and Le$^b$, sulfated glycoprotein type A of porcine gastric mucous membrane, sulfated glycoprotein active substance type H(O) of porcine gastric mucous membrane and human erythrocyte H$_1$ antigen.

23. The process as claimed in claim 18 or 20, wherein said labelled lectin is a lectin labelled with an enzyme selected from the group consisting of glucoamylase, glucose oxidase, peroxidase, alkaline phosphatase, $\beta$-galactosidase and hemeoctapeptide.

24. The process as claimed in claim 18 or 20, wherein said labelled lectin is a lectin labelled with a fluorescent substance selected from the group consisting of fluorescein isocyanate, rhodamine and dansyl chloride.

25. The process as claimed in claim 18 or 20, wherein said labelled lectin is a lectin labelled with a radioactive substance selected from the group consisting of radioactive iodine and tritium.

26. The process as claimed in claim 18, wherein said TAG in blood serum or blood plasma and an insolubilized porcine gastric mucous membrane (PGM), insolubilized by radiation-induced polymerization with a hydroxyethyl methacrylate (HEMA) or polystyrene bead, are competitively reacted with peroxidase labelled LTL.

27. The process as claimed in claim 19, wherein said TAG in blood serum or blood plasma and $^{125}$I-PGM are competitively reacted with LTL.

28. The process as claimed in claim 20, wherein said TAG in blood serum or blood plasma is reacted with LTL-agarose and the resulting complex is further reacted with peroxidase labelled LTL.

29. A method for diagnosing cancer, comprising measuring the level of tumor-associated glycolinkage in body fluid of a subject according to the method described in any one of claims 1, 15, 12, 14, 16, 21, 26, 27 or 28 and comparing the thus-measured level with that of a person in normal health.

30. A kit for determining TAG level in a body fluid comprising AG-binding lectin or L-fucose-binding lectin as a specific agglutinating agent for TAG.

31. The kit as claimed in claim 30, wherein said specific agglutinating agent is AG-binding lectin.

32. The kit as claimed in claim 30, wherein said specific agglutinating agent is L-fucose binding lectin.

* * * * *